(12) United States Patent
Kress et al.

(10) Patent No.: US 10,309,908 B2
(45) Date of Patent: Jun. 4, 2019

(54) LIGHT FIELD ILLUMINATION CONTAINER INSPECTION SYSTEM

(71) Applicant: Applied Vision Corporation, Cuyahoga Falls, OH (US)

(72) Inventors: Michael Leo Kress, Uniontown, OH (US); Bryan Murdoch, Stow, OH (US)

(73) Assignee: Applied Vision Corporation, Cuyahoga Falls, OH (US)

( * ) Notice: Subject to any disclaimer, the term of this patent is extended or adjusted under 35 U.S.C. 154(b) by 50 days.

(21) Appl. No.: 15/404,148

(22) Filed: Jan. 11, 2017

(65) Prior Publication Data

US 2018/0195974 A1 Jul. 12, 2018

(51) Int. Cl.
| | |
|---|---|
| *G06T 7/00* | (2017.01) |
| *G06T 7/90* | (2017.01) |
| *G01N 21/25* | (2006.01) |
| *G01N 21/88* | (2006.01) |
| *G01N 21/90* | (2006.01) |
| *H04N 5/225* | (2006.01) |
| *H04N 5/247* | (2006.01) |
| *G01N 21/952* | (2006.01) |
| *H04N 7/18* | (2006.01) |

(52) U.S. Cl.
CPC .......... *G01N 21/90* (2013.01); *G01N 21/251* (2013.01); *G01N 21/8806* (2013.01); *G01N 21/909* (2013.01); *G01N 21/952* (2013.01); *G06T 7/001* (2013.01); *G06T 7/90* (2017.01); *H04N 5/2256* (2013.01); *H04N 5/22541* (2018.08); *H04N 5/247* (2013.01); *H04N 7/181* (2013.01); *G01N 21/9036* (2013.01); *G01N 2021/8816* (2013.01); *G01N 2021/8819* (2013.01); *G01N 2021/8822* (2013.01); *G01N 2201/062* (2013.01); *G01N 2201/12* (2013.01)

(58) Field of Classification Search
CPC .......................... G01N 21/90; G01N 21/9054; G01N 21/909; G01N 2021/9653; G01N 2021/9563

See application file for complete search history.

(56) References Cited

U.S. PATENT DOCUMENTS

| | | | |
|---|---|---|---|
| 4,691,231 A | 9/1987 | Fitzmorris et al. | |
| 4,776,466 A * | 10/1988 | Yoshida | B07C 5/3408 209/565 |

(Continued)

FOREIGN PATENT DOCUMENTS

JP 2010146082 A * 7/2010

OTHER PUBLICATIONS

"International Search Report and Written Opinion for PCT Patent Application No. PCT/US18/12328", dated Mar. 26, 2018, 14 pages.

*Primary Examiner* — Jamie J Atala
*Assistant Examiner* — Michael Robert Cammarata
(74) *Attorney, Agent, or Firm* — Medley, Behrens & Lewis, LLC

(57) ABSTRACT

Described herein are various technologies pertaining to an automated light field illumination container inspection. The container inspection system includes a plurality of cameras that capture images of a container when the container is illuminated by way of light field illumination. Bands in images that include reflections in the exterior surface of the sidewall are identified, and a determination is made as to whether the container is defective based upon the identified bands.

20 Claims, 9 Drawing Sheets

(56) References Cited

U.S. PATENT DOCUMENTS

| | | | | |
|---|---|---|---|---|
| 5,095,204 A * | 3/1992 | Novini | G01N 21/9045 | |
| | | | 250/223 B | |
| 5,495,429 A * | 2/1996 | Craven | G01J 3/10 | |
| | | | 382/157 | |
| 5,510,610 A * | 4/1996 | Baldwin | G01N 21/9045 | |
| | | | 209/526 | |
| 5,934,440 A * | 8/1999 | Kroghrud | B07C 5/126 | |
| | | | 194/212 | |
| 5,982,941 A * | 11/1999 | Loveridge | H04N 1/409 | |
| | | | 382/154 | |
| 5,987,161 A * | 11/1999 | Doane | G06T 7/001 | |
| | | | 382/145 | |
| 6,404,516 B1 | 6/2002 | Edgar | H04N 1/00909 | |
| | | | 358/450 | |
| 6,781,620 B1 | 8/2004 | Keyes | | |
| 7,187,797 B2 | 3/2007 | Sones et al. | | |
| 9,199,757 B2 * | 12/2015 | Kolb | B65C 9/067 | |
| 9,898,813 B2 * | 2/2018 | Stuwe | G06T 7/0004 | |
| 9,916,640 B2 * | 3/2018 | Swanson | G06T 3/4038 | |
| 2001/0048524 A1 | 12/2001 | Sones et al. | | |
| 2002/0113882 A1* | 8/2002 | Pollard | H04N 1/00835 | |
| | | | 348/239 | |
| 2002/0191834 A1* | 12/2002 | Fishbaine | G01B 11/2518 | |
| | | | 382/150 | |
| 2003/0184740 A1* | 10/2003 | Paradis | G01N 21/8806 | |
| | | | 356/237.1 | |
| 2004/0150815 A1* | 8/2004 | Sones | G01N 21/9054 | |
| | | | 356/239.4 | |
| 2006/0104494 A1 | 5/2006 | Collins et al. | | |
| 2006/0126060 A1 | 6/2006 | Colle et al. | | |
| 2009/0278925 A1* | 11/2009 | Koval | G01B 11/245 | |
| | | | 348/92 | |
| 2009/0294674 A1* | 12/2009 | Bathelet | B07C 5/122 | |
| | | | 250/340 | |
| 2010/0085426 A1 | 4/2010 | Diehr et al. | | |
| 2013/0258368 A1 | 10/2013 | Shigemoto et al. | | |
| 2014/0174127 A1* | 6/2014 | Dalstra | G01N 25/72 | |
| | | | 65/29.11 | |
| 2015/0269707 A1* | 9/2015 | Swanson | G06T 3/4038 | |
| | | | 382/284 | |
| 2016/0321796 A1 | 11/2016 | Dordoni et al. | | |
| 2016/0373637 A1* | 12/2016 | Zhou | H04N 5/217 | |
| 2016/0379355 A1* | 12/2016 | Stuwe | G01N 21/90 | |
| | | | 382/141 | |
| 2018/0172602 A1* | 6/2018 | Beck | G01N 21/958 | |

* cited by examiner

LIGHT FIELD ILLUMINATION CONTAINER INSPECTION SYSTEM

BACKGROUND

Production plants for manufacturing containers (such as beverage cans) can produce a very large number of containers, with sophisticated (multicolor) decoration thereon, in a relatively short amount of time. For instance, a conventional decorator in a container production plant can decorate 2,000 containers per minute. Container decorations have intrinsic value, as consumers tend to attach perceptions of quality to a product based upon the design on the container that holds the product.

Conventionally, there is a lack of robust inspection of exterior surfaces of containers at these container production plants. A known process for container inspection is tasking an operator at the plant with periodically pulling containers from a conveyor for visual inspection. For instance, every so often (e.g., every 15 minutes), the operator may be tasked with pulling a small number of containers from the conveyor and visually inspecting the containers to ensure that the exterior surfaces of the containers are free of readily apparent defects (e.g., to ensure that proper colors are applied to the exterior surfaces of the containers, to ensure that the exterior surfaces of the containers are free of smears, etc.). Using this conventional approach, thousands of defective containers may be manufactured prior to the operator noticing a defect on the exterior surface of one or more of the sampled containers. In practice, these (completed) containers must be scrapped, resulting in significant cost to the container manufacturer.

Recently, automated systems have been developed and deployed in container production plants, wherein such systems are configured, through automated visual inspection, to detect defects on exterior surfaces of containers. These systems include multiple cameras that are positioned to capture images of exterior surfaces of a container when the container passes through an inspection region. In such systems, the images are captured while a container is illuminated by way of dark field illumination. Images of the sidewall of the container taken under dark field illumination are well-suited at depicting spatial defects, three-dimensional defects (e.g., dents, scuffs, contamination, etc.), and subtle color shifts in opaque inks on the container. A computing system analyzes the images captured by the cameras to determine whether the exterior surface of the container includes a defect. Systems that incorporate dark field illumination, however, are unable to accurately correlate measured color in the images to offline measurement systems and standards. Further, these systems are generally incapable of detecting, on containers that have been decorated with ink of dark colors, scratches or unintentional voids in decorations (where, for some reason, ink was not applied where it should have been applied).

SUMMARY

The following is a brief summary of subject matter that is described in greater detail herein. This summary is not intended to be limiting as to the scope of the claims.

Described herein is a container inspection system that is configured to ascertain whether a container being transported on a conveyor includes a defect on an exterior surface of a sidewall of the container. The container inspection system can detect defects that may occur in a design or label on an exterior surface of the container, such as an improper color being printed on the exterior surface of the container (e.g., a color shade is incorrect), smearing, and so forth, such that the design or label does not appear as desired. The container inspection system can detect various defects on exterior surfaces of containers, including physical defects (e.g., scratches, dents, etc.) or voids in decorations (e.g., where a portion of a container should be covered by ink but instead is bare metal).

The container inspection system includes an inspection dome, wherein the container is located in the inspection dome when the container is inspected. The inspection dome limits an amount of light, external to the inspection dome, that can illuminate the container (and additionally prevents light used to illuminate the exterior surface of the container from exiting the inspection dome). Further, the container inspection system includes a light source that is configured to emit light within the inspection dome. In an example, the light source can include a light emitting diode (LED) or other suitable source of light. The light source diffusely emits light, resulting in a relatively uniform light field throughout the interior of the inspection dome (such that the container is illuminated by light field illumination, rather than dark field illumination). The container inspection system includes several cameras (positioned to surround the container under inspection) that are configured to simultaneously generate images of the exterior surface of the sidewall of the container while such surface is being illuminated in the inspection dome. More specifically, the light source is strobed, such that the aforementioned container surface is illuminated for a relatively short amount of time (e.g., on the order of tens of microseconds). The cameras capture respective images of the exterior surface of the sidewall of the container while such surface is being illuminated.

The container inspection system also includes a computing system that is in communication with the cameras, wherein the computing system is configured to, for each container passing through the inspection dome, receive images (generated by the cameras) of an external surface of a sidewall of the container. The computing system determines whether the exterior surface of the sidewall of the container includes a defect based upon the images. It can be ascertained that the inspection dome includes several apertures therein: two apertures for container transport (a first aperture where the container enters the inspection dome on the conveyor, and a second aperture where the container exits the inspection dome on the conveyor), and an aperture for each camera. Further, containers are close to one another on the conveyor. Hence, images of the exterior surface of the sidewall of the container may include reflections of the apertures, as well as reflections of adjacent containers on the conveyor.

In an example, several cameras simultaneously capture respective images of the exterior surface of the sidewall of the container while the container is in the inspection dome. When the container being inspected is cylindrical, the computing system can process each image, such that the portion of the exterior surface of the sidewall of the container captured in each image is "flattened". Subsequently, the computing system can identify, in a first image of the exterior surface of the sidewall of the container (where the first image is captured by a first camera), a first region that includes reflections (e.g., from the apertures or adjacent containers on the conveyor). The computing system can replace the first region in the first image with a second region in a second image of the exterior surface of the sidewall of the container (where the second image is captured by a second camera), where the first region and the second region map to a same physical region of the exterior surface of the sidewall of the container. It can be ascertained that the second region of the second image will not depict the reflections found in the first region of the first image, since the first and second images are captured by cameras at different positions relative to the container. Moreover, these regions in the images can be identified before the images are captured based upon known geometry of the container and positions of the cameras relative to the container when the images are captured.

Responsive to replacing the first region of the first image with the second region from the second image, the first image becomes a reflection-free image of the exterior surface of the sidewall of the container. The computing system performs this process for each image captured by each camera, thereby creating several reflection-free images. The computing system can optionally stitch the reflection-free images together, thereby creating an image of the container as if the container were unwrapped (referred to as an unwrapped image). The computing system can then align the unwrapped image to a statistical model that represents an unwrapped container that is free of defects.

Thereafter, the computing system compares the unwrapped image with the statistical model. When the computing system compares the unwrapped image with the statistical model and identifies a sufficient dissimilarity therebetween, the computing system can output a signal that indicates that the container is defective. Conversely, when there is sufficient similarity between the unwrapped image and the statistical model, the computing system can output a signal that indicates that the container is non-defective.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
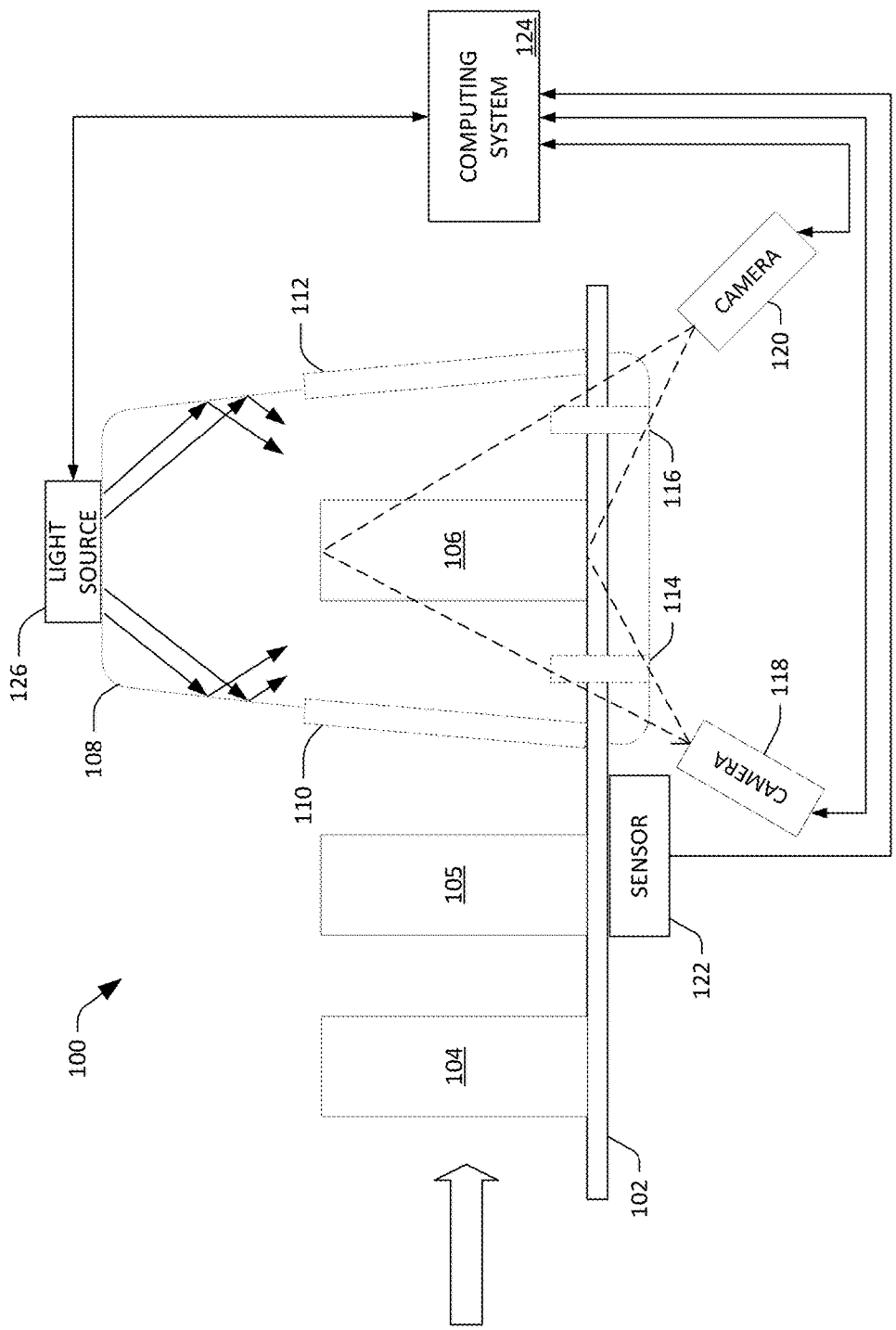
FIG. 1 is a schematic of an exemplary light field illumination container inspection system.

Various technologies pertaining to a container inspection system that incorporates light field illumination are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something, and is not intended to indicate a preference.

Further, as used herein, the terms "component" and "system" are intended to encompass instructions stored in computer-readable data storage that are configured to cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Described herein are features pertaining to identifying defects in a sidewall of a container, wherein an exterior surface of the sidewall of the container is at least somewhat reflective. Further, when reference is made to detecting defects in the sidewall of the container, such action is also intended to encompass detecting defects in labels applied to the sidewall of the container (such as a shrink-wrap label or paper label). In an example, the container may be decorated with ink and/or comprise a highly reflective material (such as bare metal). In other examples, the container glass, plastic, or paper containers, and/or have plastic or paper labels applied thereto.

The container inspection system described herein, on contrast to conventional container inspection systems, uses light field illumination to illuminate a container under inspection (where conventional container inspection systems employ dark field illumination to illuminate a container under inspection). With respect to light-field illumination, a specular surface appears white in an image captured by a camera, because some of the illumination reflects directly back towards the image sensor of the camera that captures the image. With respect to dark-field illumination, a specular surface appears black in an image captured by the camera, because the illumination is directed such that light reflects away from the image sensor of the camera that captures the image. Due at least partially to the use of light field illumination to illuminate containers, the container inspection system is well-suited to accurately correlate measured colors of inspected containers to offline color measure standards. Further, the container inspection system is configured to identify, for instance, scratches or (unintentional) voids in decoration on exterior surfaces of containers decorated with dark colors (blue, purple, etc.).

Summarily, the container inspection system includes multiple cameras that simultaneously capture images of an exterior surface of a sidewall of a container that is under inspection. The cameras are positioned such the cameras surround the container when the images are captured. The container inspection system further includes a computing system that is configured to identify, in each of the images, at least one region that is known to include reflections. Thus, in a first image captured by a first camera, the computing system identifies a region that is known to include reflections (this region can be known based upon geometries of the container inspection system, such as size and shape of the container, positions of the cameras relative to the container, detected distance between the container and an adjacent container on a conveyor, etc.). The computing system can replace the region in the first image with a region from a second image (captured by a second camera), where the region from the second image and the region from the first image map to the same physical region on the exterior surface of the sidewall of the container. Thus, the computing system effectively causes the first image to be free of reflections. Upon the computing system performing such processing (for each image captured by the cameras), the computing system can employ conventional image processing techniques to determine whether the container is defective.

With reference now to FIG. 1, an exemplary light field illumination container inspection system 100 is illustrated. For example, the system 100 can be configured to detect defects in metal containers (e.g., metal cans), plastic containers (e.g., bottles) and/or labels (paper or plastic) appended thereto. Further, the system 100 can be configured to detect defects in exterior surfaces of sidewalls of containers that comprise material (e.g., aluminum, steel, etc.) that reflects light in a specular manner. In other words, the system 100 is well-suited to detect defects in containers that are reflective. Additionally, the system 100 can be configured to detect defects in containers (e.g., metal cans) that have been decorated with ink, particularly translucent ink. Moreover, the system 100 can be configured to detect printing defects in labels applied to containers, wherein the labels are made of material that is somewhat reflective or painted with ink that is somewhat reflective. Further, while the containers depicted herein have a cylindrical sidewall, it is to be understood that the system can be configured to detect defects in sidewalls of varying shapes.

Also, the system 100 can be configured to detect defects in text or graphics printed on sidewalls of containers. The system 100 can also detect defects that may occur in a design or label on an exterior surface of the container, such as an improper color being printed on the exterior surface of the container (e.g., a color shade is incorrect), smearing, and so forth, such that the design or label does not appear as desired. For example, the system 100 can be configured to detect that a container has a design printed thereon that includes an insufficient amount of a color. Additionally, the system 100 can be configured to detect defects on exterior surfaces of containers, including physical defects (e.g., scratches, dents, etc.) or voids in decorations (e.g., on containers and/or labels that have been decorated with dark colors).

A conveyor 102 transports a plurality of containers 104-106 through an inspection dome 108. The inspection dome 108 comprises an entry aperture 110 for the plurality of containers 104-106 to enter the inspection dome 108. The inspection dome 108 further comprises an exit aperture 112 for the plurality of containers 104-106 to exit the inspection dome 108. Additionally, the inspection dome 108 comprises a first color camera aperture 114 and a second color camera aperture 116. The system 100 further comprises a first color camera 118 and a second color camera 120, wherein the cameras 118 and 120 are positioned in the apertures 114 and 116, respectively. Thus, the cameras 118 and 120 are positioned to capture images of the plurality of containers 104-106 as the plurality of containers 104-106 are transported through the inspection dome 108 by the conveyor 102. Details regarding operation of the first color camera 118 and the second color camera 120 are set forth below.

The interior surface of the inspection dome 108 is formed of material (e.g., plastic) that prevents light, external to the inspection dome 108, from illuminating containers when the containers are in the inspection dome 108. Additionally, the inspection dome 108 prevents light from exiting the inspection dome 108. Due to apertures in the inspection dome 108 (e.g., the entry aperture 110, the first camera aperture 114, etc.), a limited amount of light (that is external to the system 100) from the apertures 110-116 can illuminate the containers within the inspection dome 108. Further, the interior surface of the inspection dome 108 can be reflective. For instance, the interior surface of the inspection dome 108 can be white (e.g., painted white or formed of a white plastic).

The system 100 further comprises a sensor 122 that outputs a signal that is indicative of when a container (e.g., the first container 106) has reached an inspection region in the inspection dome 108. As will be described herein, the cameras 118 and 120 are configured to simultaneously capture images of the first container 106 when the first container 106 is in the inspection region. For example, and not by way of limitation, the sensor 122 may be a presence sensor that can detect when the first container 106 has passed a particular point (e.g., when the first container 106 has entered the inspection dome 108). Additionally or alternatively, the sensor 122 may be a rotary sensor that is configured to output data based upon movement of the conveyor 102. The output data, therefore, is indicative of a position of the first container 106 relative to a previous position of the first container 106 on the conveyor 102 and, thus, the position of the first container 106 relative to the inspection region in the inspection dome 108.

The system further comprises a computing system 124 that receives the signal output by the sensor 122. The computing system 124 can receive the signal from the sensor 122 by way of a wireless or wireline connection. The system further comprises a light source 126 that is configured to cause a sidewall of the first container 106 to be illuminated when it is within the inspection region of the inspection dome 108. The light source 126 can include an array of light emitting diodes (LEDs), wherein each LED emits white light. More particularly, the light source 126 diffusely emits light, resulting in a relatively uniform light field throughout the interior of the inspection dome 108 (such that the first container 106 is illuminated by way of light field illumination, rather than dark field illumination). By way of example, as the light source 126 diffusely emits light, the light reflects off the reflective interior wall of the inspection dome 108, resulting in a relatively uniform light field throughout the inspection dome 108 (e.g., light is incident upon the exterior surface of the sidewall of the first container 106 at various angles due to the light being diffusely emitted from the light source 126 and "bouncing around" in the inspection dome 108). The computing system 124 controls the light source 126, such that the light source 126 strobes responsive to the computing system 124 ascertaining that the first container 106 is in the inspection region in the inspection dome 108.

Position and operation of the first color camera 118 and the second color camera 120 are now set forth in greater detail. The first camera 118 and the second camera 120 are placed external to the inspection dome 108 and directed radially inwards towards a central axis of the inspection dome 108 through the first camera aperture 114 and second camera aperture 116, respectively. The first camera 118 and the second camera 120 are in communication with the computing system 124. More specifically, the first camera 118 and the second camera 120 are controlled by the computing system 124, such that the first camera 118 and second camera 120 (simultaneously) capture images of the exterior surface of the sidewall of the first container 106 when the central axis of the first container 106 is aligned with the central axis of the inspection dome 108. Likewise, the computing system 124 causes the light source 126 to emit light when the central axis of the first container 106 is aligned with the central axis of the inspection dome 108.

Since the light field is approximately uniform throughout the inspection dome 108 when the cameras 118 and 120 capture images of the exterior surface of the sidewall of the container 106, the images are taken under light field illumination. Accordingly, (1) color in the images correlates to offline measurement systems and standards; and (2) scratches or voids in decorations on the first container 106 when the first container 106 is decorated using dark colors (blue, purple, etc.) are visible in the images. Because, however, the exterior surface of the sidewall of the first container 106 is at least partially reflective, unwanted reflections may appear in images captured by the cameras 118 and 120. For example, an image of the exterior of the sidewall of the first container 106 captured by the camera 118 may include a reflection of the entry aperture 110 and a reflection of the camera aperture 114. Additionally, while FIG. 1 depicts the first container 106 as being the only container in the inspection dome 108, there may be multiple containers in the inspection dome 108 when the first container 106 is in the inspection region, and containers adjacent to the first container 106 on the conveyor 102 may be very close to the first container 106. Therefore, for instance, the image of the exterior sidewall of the first container 106 captured by the first camera 118 may include an unwanted reflection of the second container 105. As will be described below, the computing system 124 can be configured to process images captured by the cameras 118 and 120 to remove regions of the images that include unwanted reflections and replace such regions with regions of images captured by other cameras, where the replacement regions do not include unwanted reflections (and where the replacement regions map to the same physical locations on the exterior sidewall of the first container 106 as the replaced regions).

Figure 2:
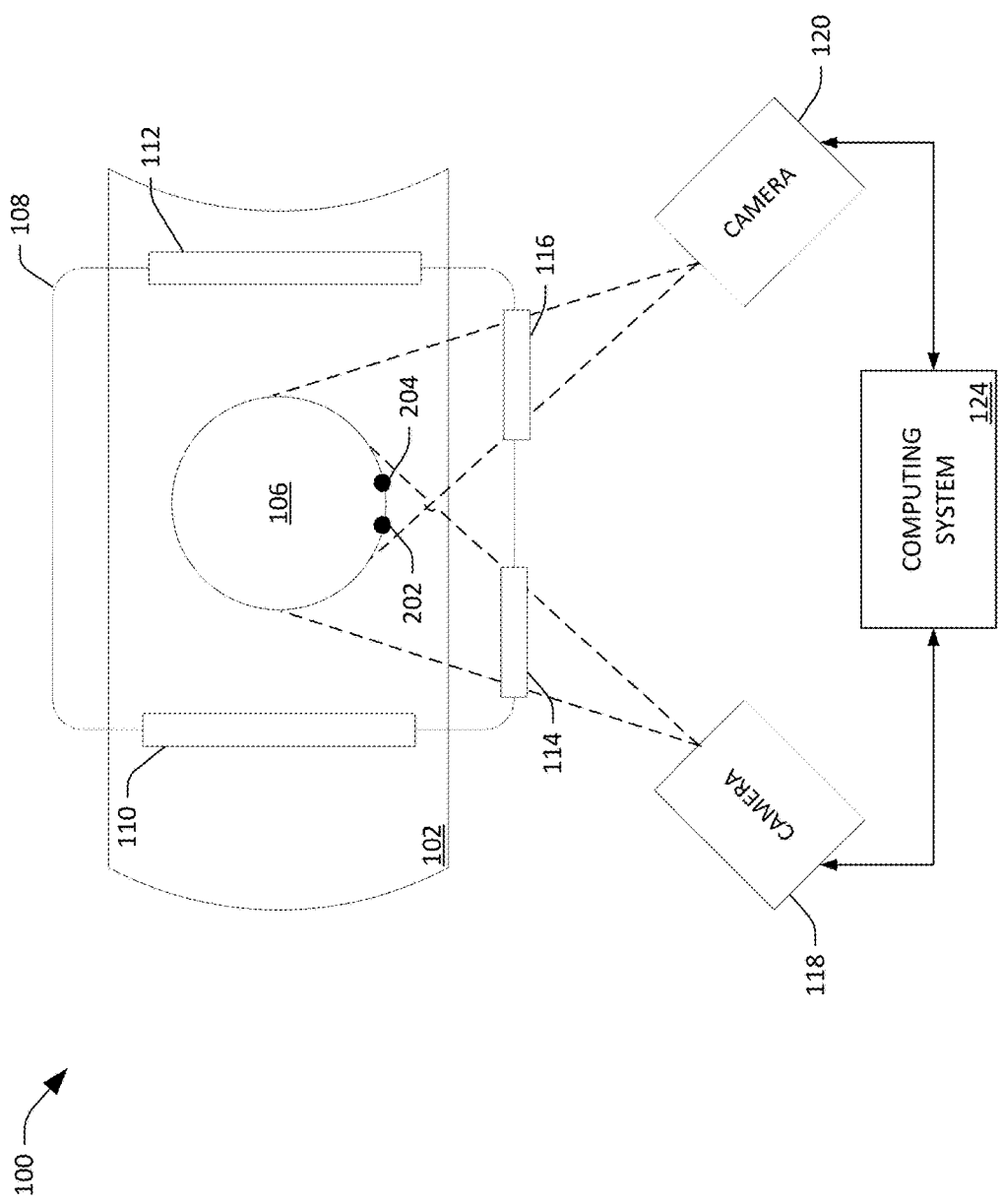
FIG. 2 is a top-down view of an exemplary light field illumination container inspection system.

With reference to FIG. 2, an overhead view of the exemplary light field illumination container inspection 100 is illustrated, wherein the first container 106 is in the inspection region of the inspection dome 108. As depicted in FIG. 2, due to the relative positions of the first camera 118, the first container 106, and the first camera aperture 114, a first reflection 202 of the first camera aperture 114 is captured in an image of the exterior sidewall of the first container 106 taken by the first camera 118. Similarly, due to the relative positions of the second camera 120, the first container 106, and the first camera aperture 114, a second reflection 204 of the first camera aperture 114 is captured in an image of the exterior sidewall of the first container 106 taken by the second camera 120. While not illustrated here, it is to be understood that other reflections may be captured in images taken by the cameras 118 and 120 (e.g., the image taken by the first camera 118 may include a reflection of the entry aperture 110 and a reflection of the second camera aperture 116, while the image taken by the second camera 120 may include a reflection of the exit aperture 112 and a reflection of the second camera aperture 116). As illustrated, the reflections 202 and 204, in the different images, map to different physical locations on the exterior surface of the first container 106 (due to the cameras capturing the images of the first container 106 from different perspectives). Moreover, the reflections 202 and 204 appear at different locations in the images captured by the cameras 118 and 120. It can also be ascertained that since relative positions between the cameras 118 and 120 and the apertures 110-116 (as well as adjacent containers, if any) are known, regions in images captured by the cameras 118-120 that include reflections can be known a priori.

Returning to FIG. 1, the computing system 124 receives the image captured by the first camera 118 and the image captured by the second camera 120 and determines whether the exterior surface of the sidewall of the container 106 includes a defect based upon the images. As will be described in greater detail below, the computing system 124 can process each image, such that the portion of the exterior surface of the sidewall of the first container 106 captured in each image is "flattened". Subsequently, the computing system 124 can define, in a first image of the exterior surface of the sidewall of the first container 106 (captured by the first camera 118), a first region that includes the first reflection 202 (and other regions that include other reflections that may be captured in the first image). The computing system 124 can replace the first region in the first image with a second region in a second image of the exterior surface of the sidewall of the first container (captured by the second camera 120), where the first region and the second region map to a same physical region of the exterior surface of the sidewall of the first container 106. It can be ascertained that the second region of the second image does not depict the reflections found in the first region of the first image, since the first and second images are captured by cameras at different positions relative to the first container 106. This process can be repeated for every region in the first image that depict reflections, such that these regions are replaced with regions of other images that do not depict the reflections. Moreover, as noted above, these regions in the images can be identified before the images are captured based upon geometries of the container inspection system 100. Finally, it can be ascertained that regions in the first image (captured by the first camera 118) can be replaced with regions of several images captured by several different cameras (including the second camera 120).

When the regions of the first image that include reflections have been replaced with regions of other images that do not include reflections, the first image becomes a reflection-free image of the sidewall of the first container 106. The computing system 124 performs this process for each image captured by each camera, thereby creating several reflection-free images. The computing system 124 can optionally stitch the reflection-free images together, thereby creating an image of the first container 106 as if the first container 106 were unwrapped (referred to as an unwrapped image). The computing system 124 can then align the unwrapped image of the first container 106 with a statistical model that represents a container that is free of defects. Subsequently, conventional approaches can be employed to ascertain whether the sidewall of the first container 106 includes defects (where, as noted above, a defect may include an improper color hue, a bare metal defect, etc.). Additionally, as the first container 106 has been illuminated by way of light field illumination when the cameras 118 and 120 captured images of the first container, colorimetric analysis can be undertaken on the resultant unwrapped image. Therefore, in addition to identifying physical defects, the computing system 124 can identify color-related defects on the exterior sidewall of the first container 106. When the computing system 124 determines that the container is defective, the computing system 124 can output a signal that causes, for instance, the first container 106 to be removed from the conveyor 102, such that the first container 106 is prevented from being populated with content and further prevented from being made available to a consumer.

While the inspection system 100 is depicted as including the first camera 118, the second camera 120, and the single light source 126, it is to be understood that the inspection system 100 may include multiple cameras (and respective camera apertures in the inspection dome 108) positioned around the inspection dome 108. For example, the system 100 can include six cameras (and six respective camera apertures) directed radially inwards towards the center axis of the inspection dome 108. The six cameras can be symmetrically arranged about the center axis. In an example, the six cameras each capture images of the first container 106 when the center axis of the first container 106 is aligned with the center axis of the inspection dome 108, which is also when the first container 106 is illuminated by way of light field illumination. The captured images: 1) each depict portions of the sidewall of the first container 106; and 2) may include reflections of conveyor apertures or camera apertures.

Further, the inspection system 100 can be configured to perform both light field and dark field inspection of containers. For instance, the inspection system 100 can include a second light source (not shown), where the second light source can be configured to direct collimated light towards the exterior surface of the sidewall of the first container 106 (at a steep angle relative to the exterior surface of the sidewall of the first container 106). Thus, when the second light source is used to illuminate the exterior surface of the sidewall of the container 106, the exterior surface of the sidewall of the container 106 is illuminated by way of dark field illumination. In such an embodiment, the cameras 118 and 120 can each capture two images: a first image when the exterior surface of the sidewall of the first container 106 is illuminated by way of light field illumination, and a second image when the exterior surface of the sidewall of the first container 106 is illuminated by way of dark field illumination. These images can be captured closely in time (within milliseconds), wherein the container 106 is in the inspection region of the inspection dome 108 for both images. In an alternative embodiment, separate sets of cameras can be used to capture images when the container is illuminated using light field illumination and dark field illumination, respectively (where, optionally, a set of cameras used with light field illumination includes more cameras than a set of cameras used with dark field illumination). As discussed above, images of the sidewall of the first container 106 taken under dark field illumination are well-suited for use when identifying spatial defects, three-dimensional defects (e.g., dents, scuffs, contamination, etc.), and subtle color shifts in opaque inks on the first container 106. The computing system 124 can be further configured to identify these defects when the first container 106 is illuminated under dark field illumination using conventional approaches.

Figure 3:
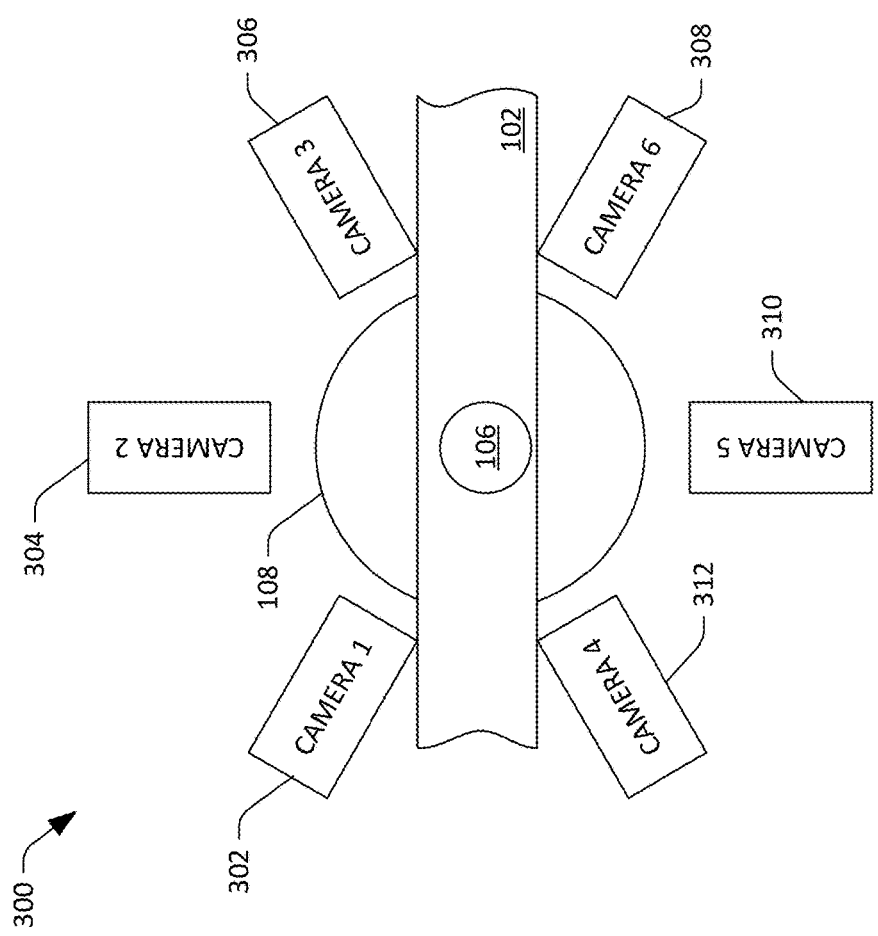
FIG. 3 is another top-down view of an exemplary light field illumination container inspection system.

Referring briefly to FIG. 3, an overhead view of an exemplary container inspection system 300 is illustrated. The container inspection system 300 comprises six cameras 302-312, arranged around the exterior of the inspection dome 108, and configured to simultaneously capture images of the container 106 when the container is illuminated in the inspection dome 108. While not shown, it is understood that the inspection dome 108 in this example includes entry and exit apertures, as well as six camera apertures. While examples set forth herein refer to the inspection system including two cameras, it has been found to be beneficial for the inspection system to have six cameras to allow for sufficient overlap between regions of the container 106 captured in images generated by adjacent cameras in the inspection system 300.

Figure 4:
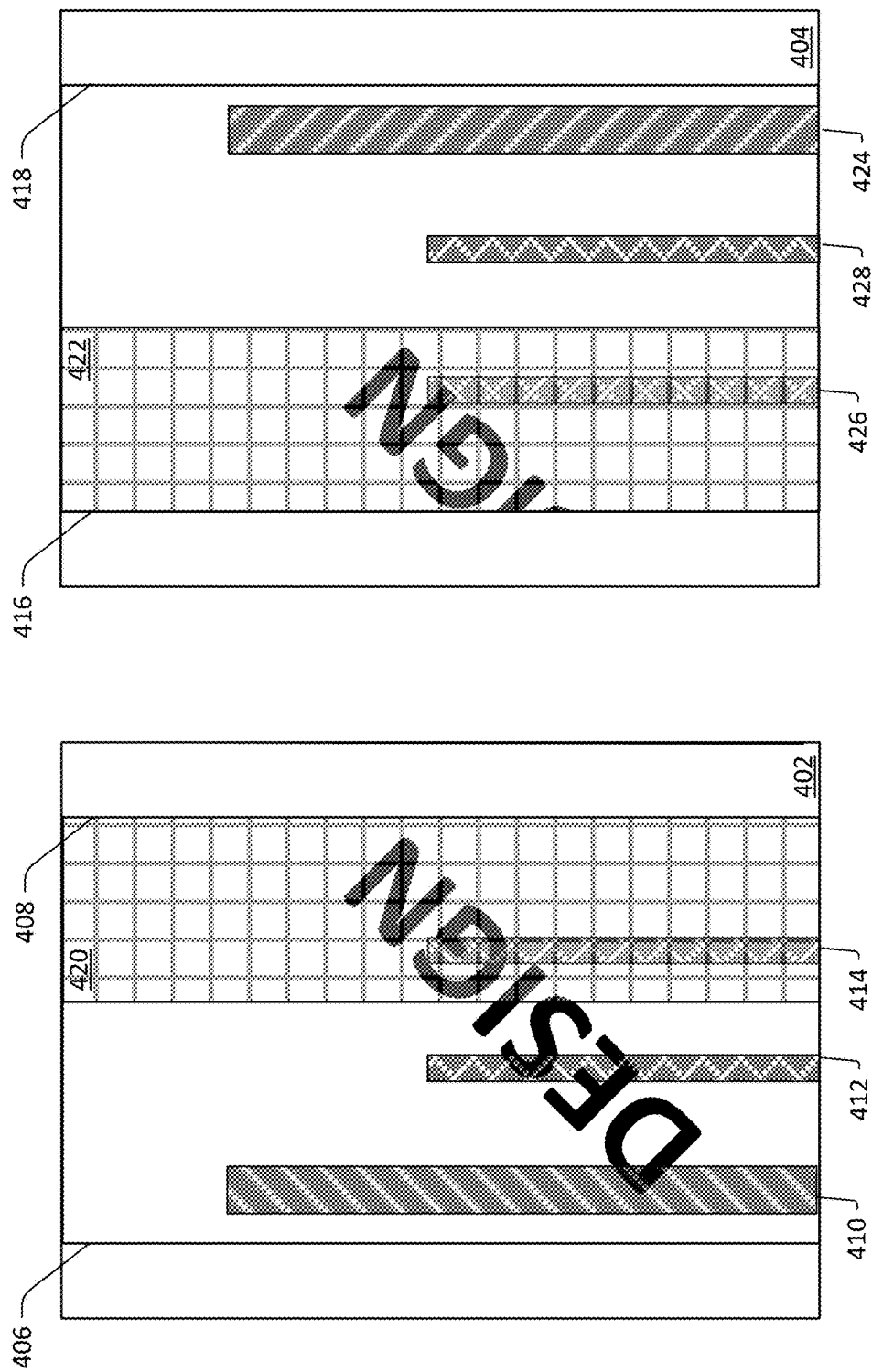
FIG. 4 depicts images of a container captured by a first camera and a second camera of a light field illumination container inspection system.

Turning now to FIG. 4, exemplary images 402-404 captured, for instance, by the first camera 118 and the second camera 120 when the first container 106 is in the inspection region of the inspection dome 108 are illustrated. The first image 402, captured by the first camera 118, depicts a portion of the exterior surface of the sidewall of the first container 106, where lines 406 and 408 depict boundaries of the first container 106 in the first image 402. The first image 402 depicts the word "DESIGN" printed on the exterior surface of the sidewall of the first container 106. The computing system 124 can identify a band 410 in the first image 402, where the band 410 includes a reflection of the entry aperture 110 visible in the first image 402. Similarly, the computing system 124 can identify bands 412 and 414 in the first image 402, where the bands 412-414 include reflections of the first camera aperture 114 and the second camera aperture 116, respectively, which are visible in the first image 402.

The second image 404, captured by the second camera 120, depicts another portion of the exterior surface of the sidewall of the first container 106, where lines 416-418 depict boundaries of the first container 106 in the second image 404. The first image 402 includes a first region 420 that depicts a portion of the sidewall of the first container 106, and the second image 404 includes a second region 422 that depicts the same portion of the sidewall of the first container 106. Thus, the regions 420 and 422 map to a same physical region of the exterior sidewall of the first container 106 (due to the cameras 118 and 120 having overlapping fields of view). Due to geometries of the first camera 118 and the second camera 120 relative to the first container 106, however, the reflections of the above-described apertures (and adjacent containers) appear at different locations on the exterior surface of the first container 106 in the images 402 and 404.

The second image 404 includes a portion of the word "DESIGN". Similar to what has been described above with respect to the first image 402, the computing system 124 can identify bands 424-428 in the second image 404, where the bands 424-428 comprise reflections of exit aperture 112 and other camera apertures.

Figure 5:
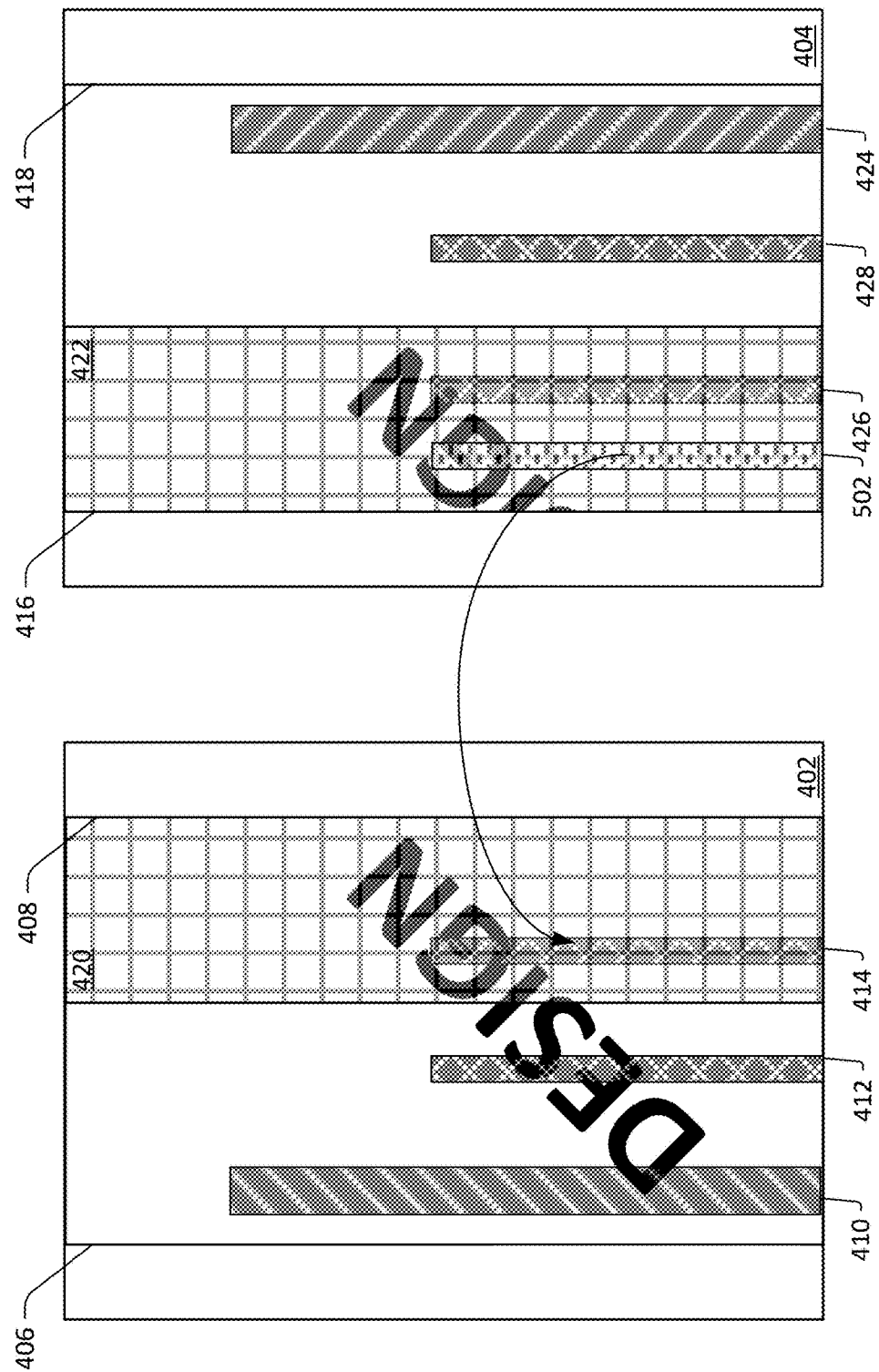
FIG. 5 depicts a band in a first image being replaced with a band from a second image.

With reference now to FIG. 5, replacement of the band 414 in the first image 402 with a band from the second image 404 is illustrated. With more specificity, the second image 404 can include a band 502, wherein the band 502 is free of reflections. Further, the band 502 corresponds to the same physical region of the exterior sidewall of the first container 106 as the band 414 of the first image 402 (which depicts a reflection). The computing system 124 can be programmed to identify that the band 414 of the first image 402 can be replaced with the band 502 of the second image 404 based upon known geometries of the inspection system 100, and can further be programmed to replace the band 414 in the first image 402 with the band 502 in the second image. The bands 410 and 412 in the first image can be replaced with bands from other images that are free of reflections, in a manner similar to what has been described above with respect to the band 502 from the second image 404 replacing the band 414 in the first image 402.

While FIG. 5 is set forth to illustrate replacement of a band in one image with a band in another image, other approaches are contemplated. As indicated previously, the computing system 124 can have knowledge of locations of the bands 410-414 in the first image 402. The computing system 124, instead of replacing the bands 410-414, can filter the bands 410-414 from the first image 402 when determining whether there is a defect in the sidewall of the first container 106. More specifically, the computing system 124 can receive the first image 402 from the first camera 118, perform image processing on the first image 118 to "flatten" the first container 106 in the first image 402 (such that the first image appears as shown in FIG. 4), and then align the first image 402 with a corresponding portion of a statistical model of a non-defective container. When comparing the first image 402 with the statistical model, the computing system 124 can filter the bands 410-414 from the first image 402, such that pixels in the bands 410-414 are not considered by the computing system 124 when determining whether the exterior surface of the sidewall of the first container 106 is defective. This process can be repeated for each image captured by cameras of the container inspection system 100; thus, even though a band that includes a region of the exterior surface of the sidewall of the first container 106 is filtered in one of the images, due to the overlapping fields of view of the cameras of the system 100, a portion of a second image that depicts a same region of the exterior sidewall of the first container 106 will be considered by the computing system 124 when determining whether the exterior sidewall of the first container 106 is defective.

Figure 6:
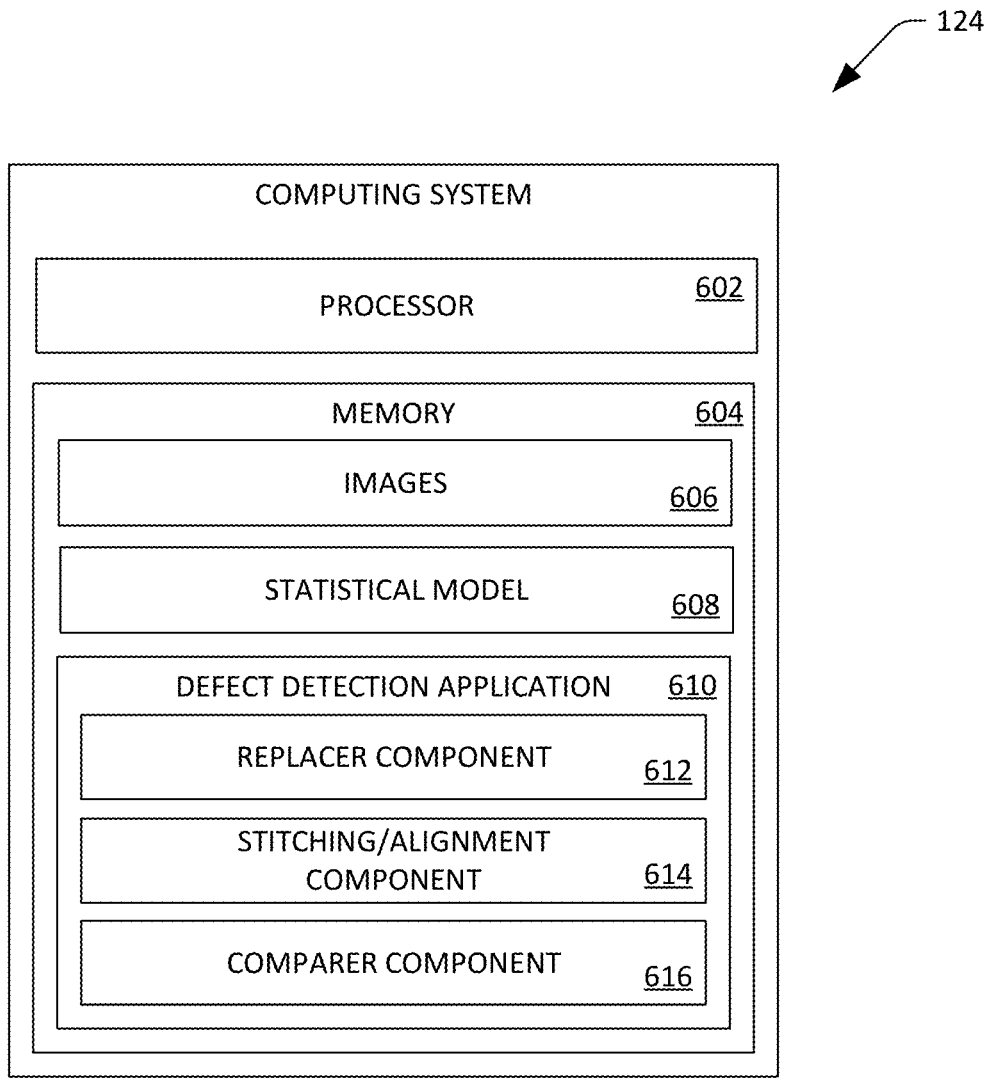
FIG. 6 depicts a functional block diagram of a computing system of a light field illumination container inspection system.

Now referring to FIG. 6, a functional block diagram of the computing system 124 is illustrated. The computing system 124 includes a processor 602 and memory 604. The memory has images 606 (generated by the cameras of the inspection system 100) loaded therein. For instance, the images 606 can comprise: 1) the image 402 captured by the first camera 118; and 2) the image 404 captured by the second camera 120, wherein the images are of the exterior surface of the sidewall of the first container 106 when illuminated by way of light field illumination.

Further, the memory has a statistical model 608 of a defect-free (and unwrapped) container loaded therein. For instance, the statistical model can comprise a plurality of pixels, and each pixel can have a distribution assigned thereto, where the distribution is indicative of values of the pixel that correspond to a non-defective container.

In an embodiment, the computing system 124 generates the statistical model 608 based upon images of a number of non-defective containers. The system 100, prior to inspecting containers, processes a preselected number of non-defective containers. With more specificity, the first camera 118 and the second camera 120 capture images of non-defective containers as such containers pass through the inspection dome 108 of the system 100. The computing system 124 forms unwrapped images of these containers as described above, and aligns the unwrapped images with one another. During alignment, the computing system 124 can perform any suitable image processing technique to create a pixel-by-pixel correspondence between unwrapped images, where each pixel has a value assigned thereto, with the value being indicative of color of the pixel. Using these pixel values, the computing system 124 can form the statistical model 608 of a container that is to be inspected, where the statistical model includes, for instance, a distribution of values for each pixel. In another embodiment, the computing system 124 can receive a template spectrophotometer measurement of a graphic and/or text that is on the exterior surface of the sidewall of the first container 106. The computing system 124 can generate the statistical model 608 based upon the spectrophotometer measurement.

The memory 604 additionally has a defect detection application 610 loaded therein. The defect detection application 610 is generally configured to ascertain whether the exterior surface of the sidewall of the first container 106 has a defect therein based upon the images 606 and the statistical model 608. As noted previously, the defect detection application 610 can be configured to identify color defects, scratches, or voids in decorations (particularly decorations with ink of dark colors). The defect detection application 610 comprises a replacer component 612, which is configured to process each image, such that the portion of the exterior sidewall of the container captured in each image is "flattened". Further, the replacer component 612 is configured to identify, for each image in the images, bands that depict reflections in the exterior surface of the sidewall of the first container 106 and bands that do not depict reflections in the exterior surface of the sidewall of the first container 106 (but that can be used to replace "reflective" bands from other images). Since the geometries of the system 100 are static (with the possible exception of distance between containers being somewhat variable), the locations of the bands in images captured by cameras of the inspection system 100 are likewise static. Responsive to identifying these bands, the replacer component 612 replaces bands in images that depicts reflections with corresponding bands from other images (as illustrated in FIG. 4), thereby forming several "reflection-free" images.

The defect detection application 610 additionally comprises a stitching/alignment component 614. Responsive to the replacer component 612 generating the "reflection-free" images, the stitching/alignment component 614 is configured to stitch these images together, such that a reflection-free image of the unwrapped first container 106 is formed (which can be referred to as an unwrapped image). The stitching/alignment component 614 is further configured to align the unwrapped image with the statistical model 608. While the description above indicates that the computing system 124 performs processing relating to reflection removal prior to processing relating to stitching, it is to be understood that the computing system 124 can alternatively be configured to stitch images together prior to replacing bands that include reflections with bands that are free of reflections. Moreover, as described above, stitching images is optional.

The defect detection application 610 additionally comprises a comparer component 616. The comparer component 616 is configured to compare reflection-free images of a sidewall of a container (partial or complete) with the statistical model 608. The comparer component 616 can compare the value of each pixel in the reflection-free image with the corresponding statistics in the statistical model, and can output signal as to whether the container 106 is defective based upon such comparison. For instance, if values of the pixels of the unwrapped image correspond to the statistics in the statistical model, the comparer component 616 can output an indication that the container 106 is not defective. Contrarily, if values of the pixels of the unwrapped image do not correspond to the statistics in the statistical model, the comparer component 616 can output a signal that the container 106 is defective.

Figure 7:
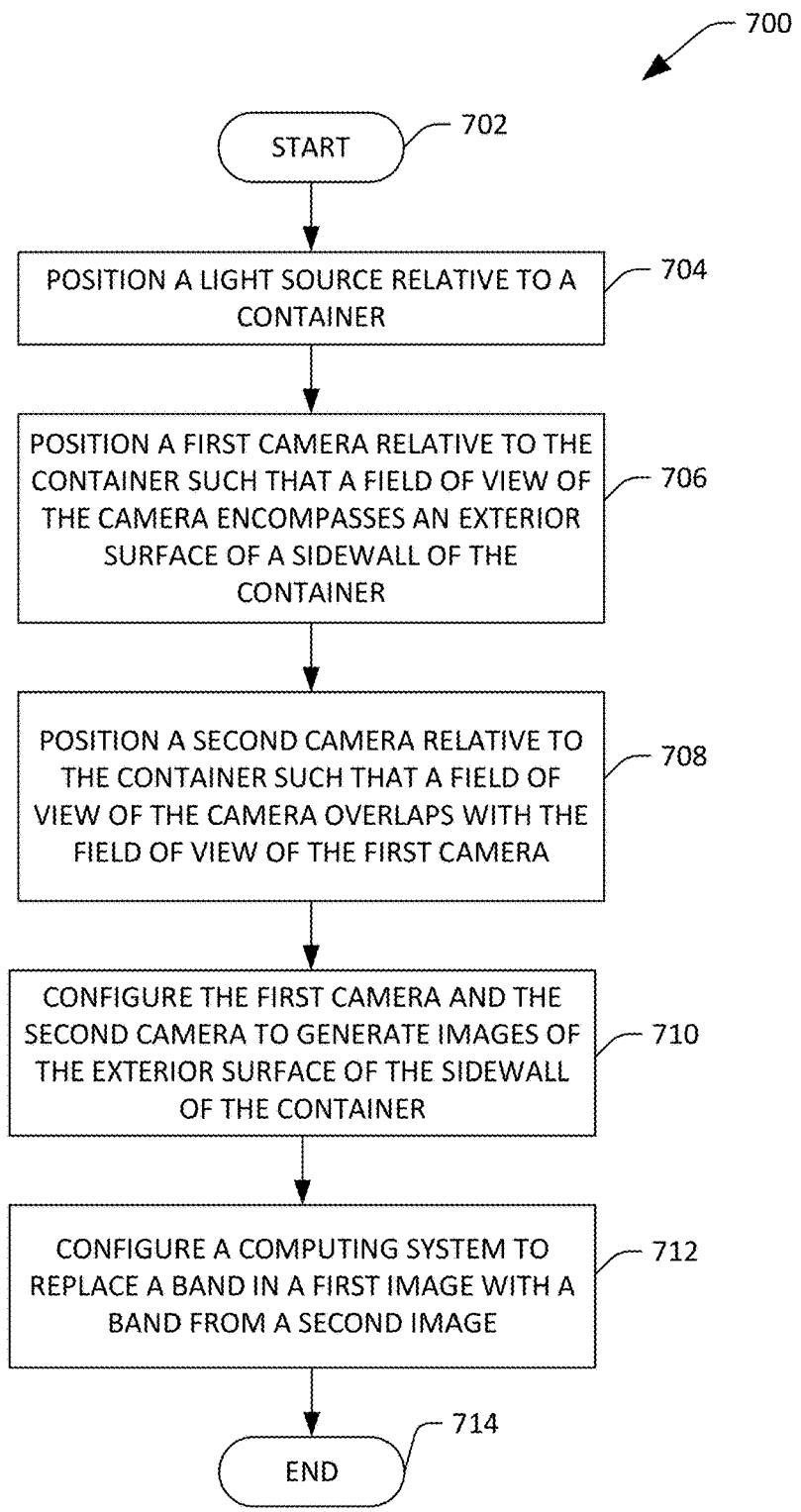
FIG. 7 is a flow diagram illustrating an exemplary methodology for configuring a light field illumination container inspection system.
Figure 8:
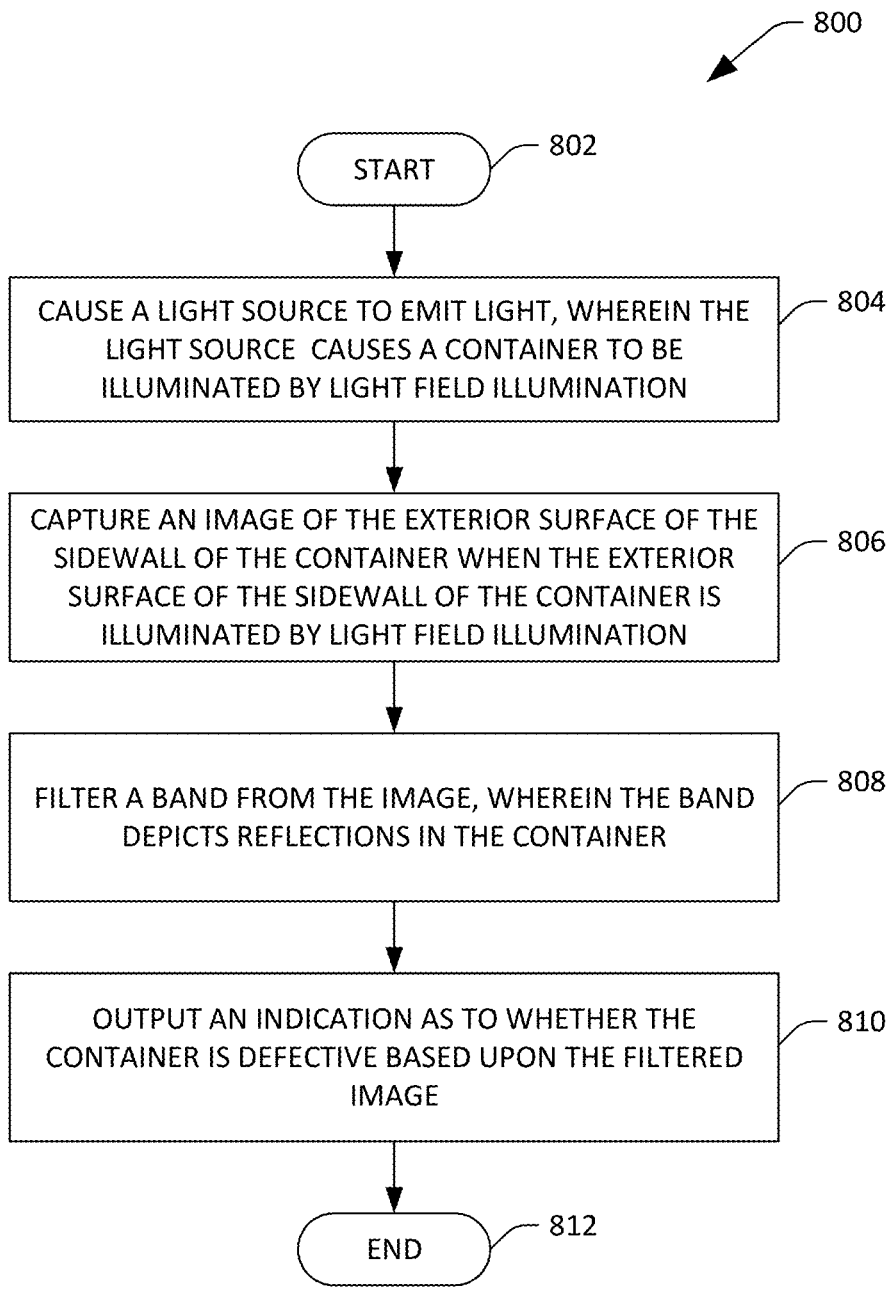
FIG. 8 is a flow diagram illustrating an exemplary methodology for operating a light field illumination container inspection system.

FIGS. 7 and 8 depict exemplary methodologies pertaining to inspection of containers. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Turning solely to FIG. 7, an exemplary methodology 700 for configuring a container inspection system that illuminates containers by way of light field illumination is illustrated. The exemplary methodology 700 starts at 702, and at 704 a light source is positioned relative to an inspection dome, such that the light source causes an exterior surface of a sidewall of a container that passes through the inspection dome to be illuminated by light field illumination.

At 706, a first camera is positioned relative to the inspection dome, such that a field of view of the first camera encompasses the exterior surface of the sidewall of the container when the external surface is illuminated by the light field illumination. The first camera is configured to capture an image of the exterior surface of the sidewall of the container when the container is being transported by a conveyor through the inspection dome of the container inspection system.

At 708, a second camera is positioned relative to the inspection dome, such that a field of view of the second camera partially overlaps with the field of view of the first camera. The second camera is configured to capture an image of the exterior surface of the sidewall of the container when the container is being transported by a conveyor through the inspection dome of the container inspection system.

At 710, the first camera and the second camera are configured to generate images of the exterior surface of the sidewall of the container when the exterior surface of the sidewall of the container is illuminated by light field illumination.

At 712, a computing system is configured to: receive the images generated by the first and the second cameras; replace a band in the first image with a band from the second image; and generate an indication as to whether or not the container is defective based upon the band in the first image being replaced with the band from the second image. The methodology 700 completes at 714.

Referring now to FIG. 8, an exemplary methodology 800 that facilitates operating a light field illumination container inspection system is illustrated. The methodology 800 starts at 802, and at 804, a light source is caused to emit light such that exterior surface of a sidewall of the container is illuminated by light field illumination. As described previously, this is performed while the container is being transported at a relatively high rate of speed along a conveyor.

At 806, an image of the exterior surface of the sidewall of the container is captured by a camera while the exterior surface of the sidewall of the container is illuminated by light field illumination. At 808, a band of the image that comprises reflections is filtered from the image, thereby creating a filtered image. At 810, the container is labeled as being either defective or non-defective based upon the filtered image. The methodology 800 completes at 812.

Figure 9:
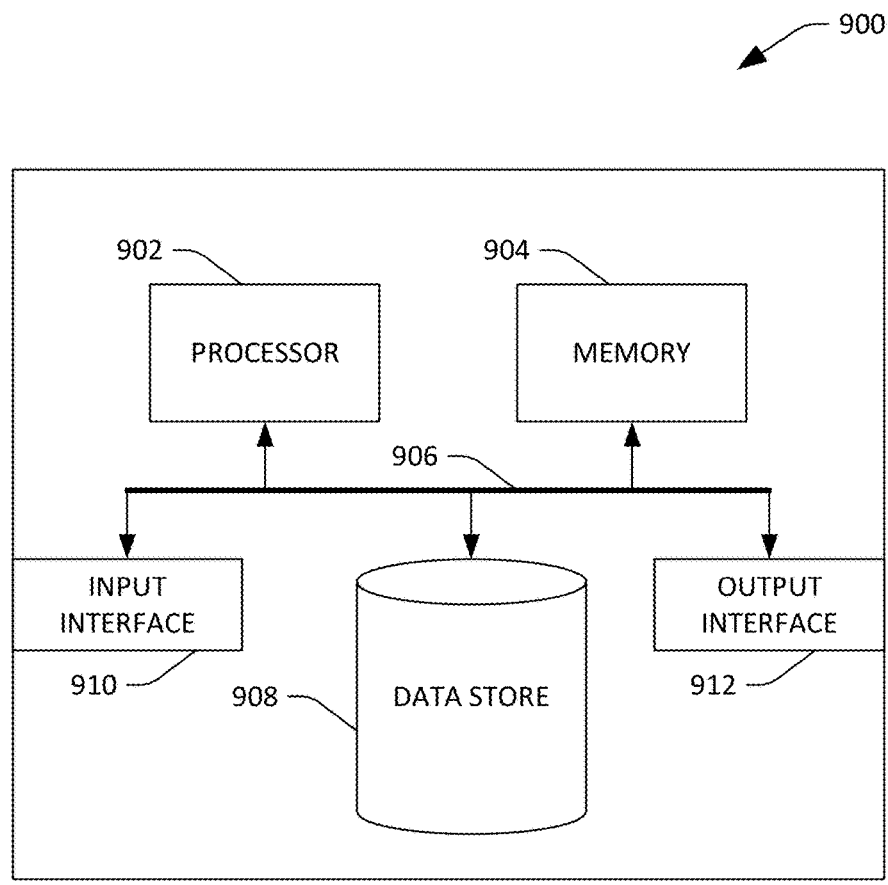
FIG. 9 is an exemplary computing device.

Referring now to FIG. 9, a high-level illustration of an exemplary computing device 900 that can be used in accordance with the systems and methodologies disclosed herein is illustrated. For instance, the computing device 900 may be used in a system that detects color defects in containers that have been decorated with ink. By way of another example, the computing device 900 can be used in a system that detects scratches or voids in decorations (particularly decorations with ink of dark colors) in containers. The computing device 900 includes at least one processor 902 that executes instructions that are stored in a memory 904. The instructions may be, for instance, instructions for implementing functionality described as being carried out by one or more components discussed above or instructions for implementing one or more of the methods described above. The processor 902 may access the memory 904 by way of a system bus 906. In addition to storing executable instructions, the memory 904 may also store images, defect signatures, etc.

The computing device 900 additionally includes a data store 908 that is accessible by the processor 902 by way of the system bus 906. The data store 908 may include executable instructions, images, etc. The computing device 900 also includes an input interface 910 that allows external devices to communicate with the computing device 900. For instance, the input interface 910 may be used to receive instructions from an external computer device, from a user, etc. The computing device 900 also includes an output interface 912 that interfaces the computing device 900 with one or more external devices. For example, the computing device 900 may display text, images, etc. by way of the output interface 912.

It is contemplated that the external devices that communicate with the computing device 900 via the input interface 910 and the output interface 912 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 900 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 900 may be a distributed system. Thus, for instance, several devices may be in communication by way of a network connection and may collectively perform tasks described as being performed by the computing device 900.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A container inspection system comprising:
   an inspection dome, wherein an interior surface of the inspection dome is reflective, and further wherein the inspection dome comprises an entry aperture and an exit aperture, wherein a conveyor transports a metal container into the inspection dome through the entry aperture, and further wherein the conveyor transports the metal container out of the inspection dome through the exit aperture;
   a light source configured to diffusely emit light in the inspection dome, such that an exterior surface of a sidewall of the metal container is illuminated by light field illumination when the metal container is in the inspection dome;
   a first camera configured to capture a first image of a first portion of the exterior surface of the sidewall of the metal container when the exterior surface is illuminated by light field illumination;
   a second camera configured to capture a second image of a second portion of the exterior surface of the sidewall of the metal container when the exterior surface is illuminated by light field illumination, wherein the first portion and second portion are partially overlapping; and
   a computing system in communication with the first camera and the second camera, wherein the computing system is configured to:
      identify a band at a first predetermined location in the first image, wherein the first predetermined location of the band is based upon a position of the first camera relative to the metal container when the first image of the metal container was captured by the first camera, wherein the band depicts a reflection in the exterior surface of the sidewall of the metal container;
      replace the band of the first image with a second band from the second image to generate a modified image, wherein the second band is at a second predetermined location in the second image, and further wherein the second predetermined location is based upon a position of the second camera relative to the metal container when the second image of the metal container was captured by the second camera; and
      output an indication as to whether the metal container is defective based upon the modified image.

2. The container inspection system of claim 1, wherein the second image is generated simultaneously with the first image.

3. The container inspection system of claim 1, wherein the computing system is further configured to:
   perform a colorimetric measurement on at least a portion of the modified image; and
   output the indication as to whether the metal container is defective further based upon the colorimetric measurement.

4. The container inspection system of claim 1, wherein the computing system is configured to output the indication based upon the second image.

5. The container inspection system of claim 1, further comprising:
   a plurality of cameras that are symmetrically arranged around the inspection dome, wherein the first camera and the second camera are included in the plurality of cameras.

6. The container inspection system of claim 5, wherein the plurality of cameras comprises at least six cameras.

7. The container inspection system of claim 1, further comprising a second light source that is configured to emit collimated light, wherein the second light source illuminates the exterior surface of the sidewall of the metal container by way of dark field illumination.

8. The container inspection system of claim 7, wherein the computing system is configured to control the light source, the second light source, and the first camera such that the first camera is additionally configured to capture a third image of the exterior surface of the sidewall of the metal container when the exterior surface of the sidewall of the metal container is illuminated by the second light source.

9. The container inspection system of claim 1, wherein the computing system is further configured to:
  generate an unwrapped image of the metal container based upon multiple images of the metal container, the multiple images of the metal container captured simultaneously when the metal container is in the inspection dome, wherein the multiple images of the metal container comprise the first image and the second image;
  align the unwrapped image of the metal container with a statistical model, the statistical model being a model of a non-defective container;
  compare the unwrapped image with the statistical model; and
  output the indication as to whether the metal container is defective based further upon the comparison.

10. A method executed by a computing device of a container inspection system, the method comprising:
  receiving, from a first camera, a first image of an exterior surface of a sidewall of a container, wherein the first camera captures the first image as the container is transported through an inspection region of the container inspection system by a conveyor;
  receiving, from a second camera, a second image of the exterior surface of the sidewall of the container, wherein the second camera captures the second image simultaneously with the first camera capturing the first image;
  responsive to receiving the first image and the second image, modifying the first image by replacing a first band of the first image with a second band from the second image, wherein the first band is at a first predetermined location in the first image and the second band is at a second predetermined location in the second image, wherein the first predetermined location is based upon a position of the first camera relative to the container when the first camera captures the first image, and further wherein the second predetermined location is based upon a position of the second camera relative to the container when the second camera captures the second image;
  responsive to modifying the first image, determining whether the container is defective based upon the first image; and
  outputting an indication as to whether the container is defective responsive to determining whether the container is defective.

11. The method of claim 10, wherein the container is cylindrical and formed of a metal.

12. The method of claim 10, further comprising:
  transmitting a control signal to a light source that diffusely emits light, wherein the light source is configured to illuminate the container by way of light field illumination when the first camera and the second camera capture the first and second images, respectively.

13. The method of claim 12, further comprising:
  receiving, from a sensor, a signal that indicates that the container is in an inspection region of an inspection dome, wherein an interior surface of the inspection dome is painted with a reflective paint; and
  transmitting the control signal based upon the signal received from the sensor.

14. The method of claim 10, further comprising:
  responsive to modifying the first image, forming an unwrapped image of the container, wherein the unwrapped image of the container is formed based upon the first image and the second image.

15. The method of claim 14, wherein the unwrapped image of the container is based upon six images simultaneously captured by six different cameras.

16. The method of claim 10, wherein the first band of the first image depicts a reflection of an aperture in an inspection dome, wherein the container is within the inspection dome when the first image and the second image were captured by the first and second camera, respectively.

17. A container inspection system comprising:
  an inspection dome, wherein an interior surface of the inspection dome is reflective, and further wherein the inspection dome comprises an entry aperture and an exit aperture, wherein a conveyor transports a container into the inspection dome through the entry aperture, and further wherein the conveyor transports the container out of the inspection dome through the exit aperture;
  a light source configured to diffusely emit light in the inspection dome, such that an exterior surface of a sidewall of the container is illuminated by light field illumination when the container is in the inspection dome;
  a first camera configured to generate a first image of a first portion of the exterior surface of the sidewall of the container when the exterior surface is illuminated by the light source;
  a second camera configured to generate a second image of a second portion of the exterior surface of the sidewall of the container when the exterior surface is illuminated by the light source, wherein the first portion and the second portion partially overlap; and
  a computing system in communication with the first camera and the second camera, wherein the computing system is configured to:
    identify a band at a first predetermined location in the first image, wherein the first predetermined location is known prior to the first camera generating the first image, the first predetermined location is based upon a position of the first camera relative to the container when the first image of the container was generated by first camera, wherein the band depicts a reflection in the exterior surface of the sidewall of the container;
    replace the band of the first image with a second band from the second image to generate a modified image, wherein the second from the second image is at a second predetermined location in the second image, and further wherein the second predetermined location is known prior to the second camera generating the second image; and
    output an indication as to whether the container is defective based upon the modified image.

18. The container inspection system of claim 17, wherein the first camera and the second camera are amongst six cameras in the container inspection system that are symmetrically arranged about a center axis of the inspection dome.

19. The container inspection system of claim 17, wherein the container is formed of a metal.

20. The container inspection system of claim 17, wherein the band and the second band are at regions of the first image and second image, respectively, where the first portion and the second portion overlap.

* * * * *